United States Patent [19]
Sjostrom et al.

[11] Patent Number: 6,090,122
[45] Date of Patent: Jul. 18, 2000

[54] SURGICAL INSTRUMENT HANDPIECE AND SYSTEM

[75] Inventors: Douglas D. Sjostrom, Reading, Mass.; Peter M. Cesarini, Londonderry, N.H.; Paul A. Torrie, Marblehead, Mass.; Graham Smith, Plaistow, N.H.; Steven Ek, Bolton, Mass.

[73] Assignee: Smith & Nephew, Inc., Andover, Mass.

[21] Appl. No.: 09/233,915

[22] Filed: Jan. 21, 1999

Related U.S. Application Data

[63] Continuation of application No. 08/630,537, Apr. 10, 1996, Pat. No. 5,871,493.
[60] Provisional application No. 60/007,117, Oct. 31, 1995.

[51] Int. Cl.$^7$ .................................................. A61B 17/14
[52] U.S. Cl. ......................................................... 606/180
[58] Field of Search ............................... 606/180, 170, 606/79, 85, 80, 173, 53, 86, 172, 87, 88, 89

[56] References Cited

U.S. PATENT DOCUMENTS

| | | |
|---|---|---|
| Re. 034,556 | 3/1994 | Sjostrom et al. . |
| D. 303,148 | 8/1989 | Rexroth et al. . |
| 2,842,131 | 7/1958 | Smith . |
| 4,188,942 | 2/1980 | Fehlberg . |
| 4,895,570 | 1/1990 | Larkin . |
| 5,133,729 | 7/1992 | Sjostrom . |
| 5,135,483 | 8/1992 | Wagner et al. . |
| 5,171,245 | 12/1992 | Cezana . |
| 5,217,478 | 6/1993 | Rexroth . |
| 5,380,333 | 1/1995 | Meloul et al. . |
| 5,487,747 | 1/1996 | Stagmann et al. . |
| 5,492,527 | 2/1996 | Glowa et al. ............................... 604/22 |
| 5,496,323 | 3/1996 | Dye . |
| 5,507,774 | 4/1996 | Holmes et al. .......................... 606/208 |

FOREIGN PATENT DOCUMENTS 1980002916221 3/1980 Germany .
1985003341876 5/1985 Germany .

OTHER PUBLICATIONS

International Search Report dated Jan. 15, 1997.
Aesculap AG, product brochure, "Integral Shaver System".
Arthrex, product brochure, "A Revolutionary New Shaver System With Quality You Can Count On"; Naples, FL 1994.
Karl Storz GmbH & Co. and Karl Storz Endoscopy, "Unidrive—A New Shaver System For Surgical Arthroscopy"; Endo World Art No. 3–E, 1994.
Linvatec Corporation, product brochure, "Presenting the Apex Universal Drive System"; Largo, FL; 1995.
Smith & Nephew Endoscopy; product catalog; "Shaver Systems"; 1996.

*Primary Examiner*—Michael Buiz
*Assistant Examiner*—Anthony King
*Attorney, Agent, or Firm*—Fish & Richardson P.C.

[57] ABSTRACT

A surgical apparatus includes a body configured for insertion into a bore of a surgical handpiece and a latch that includes a resilient member connected to the body. The resilient member has a latching structure configured to latchingly engage a surface of the surgical handpiece within the bore.

35 Claims, 17 Drawing Sheets

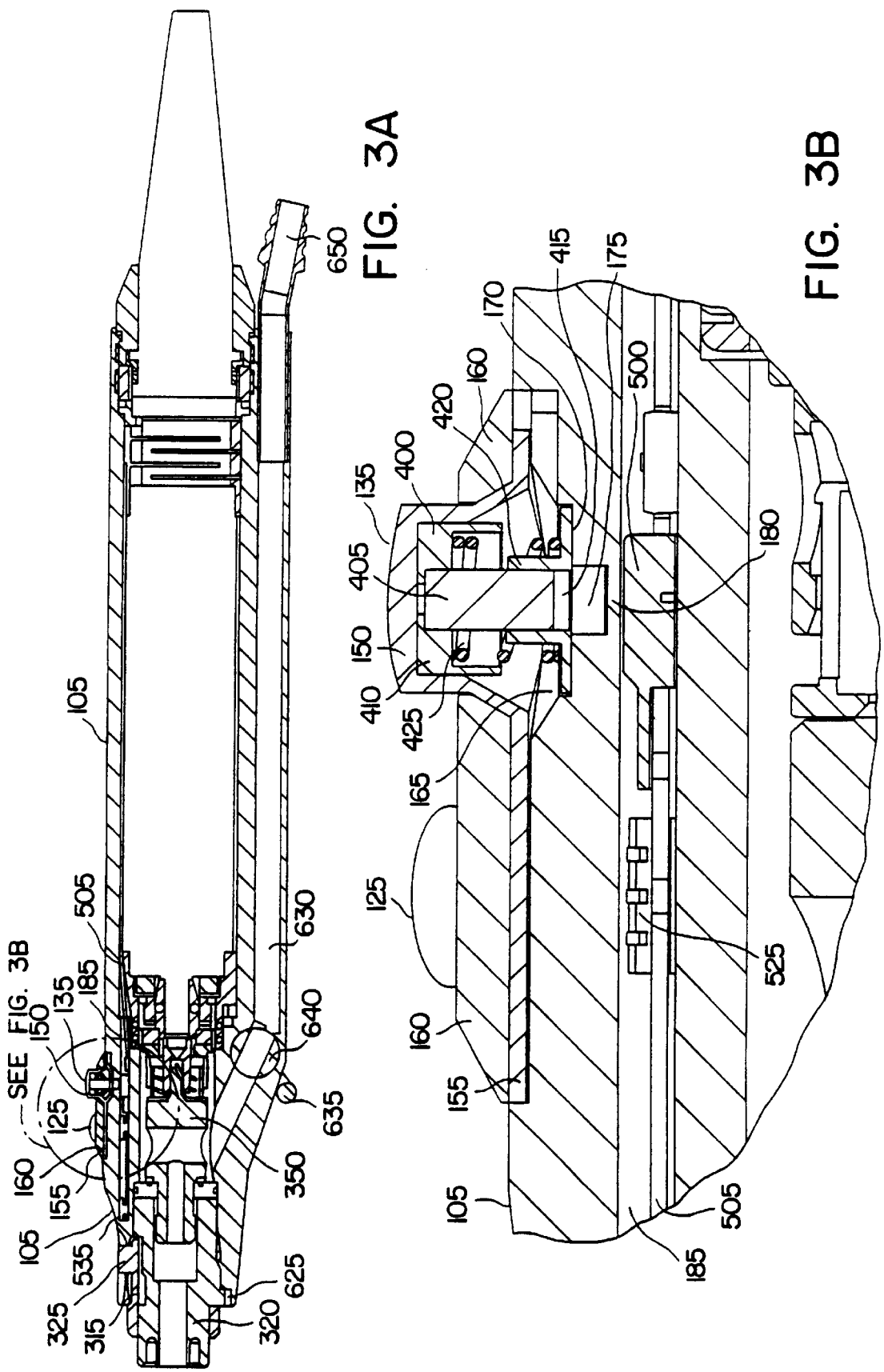

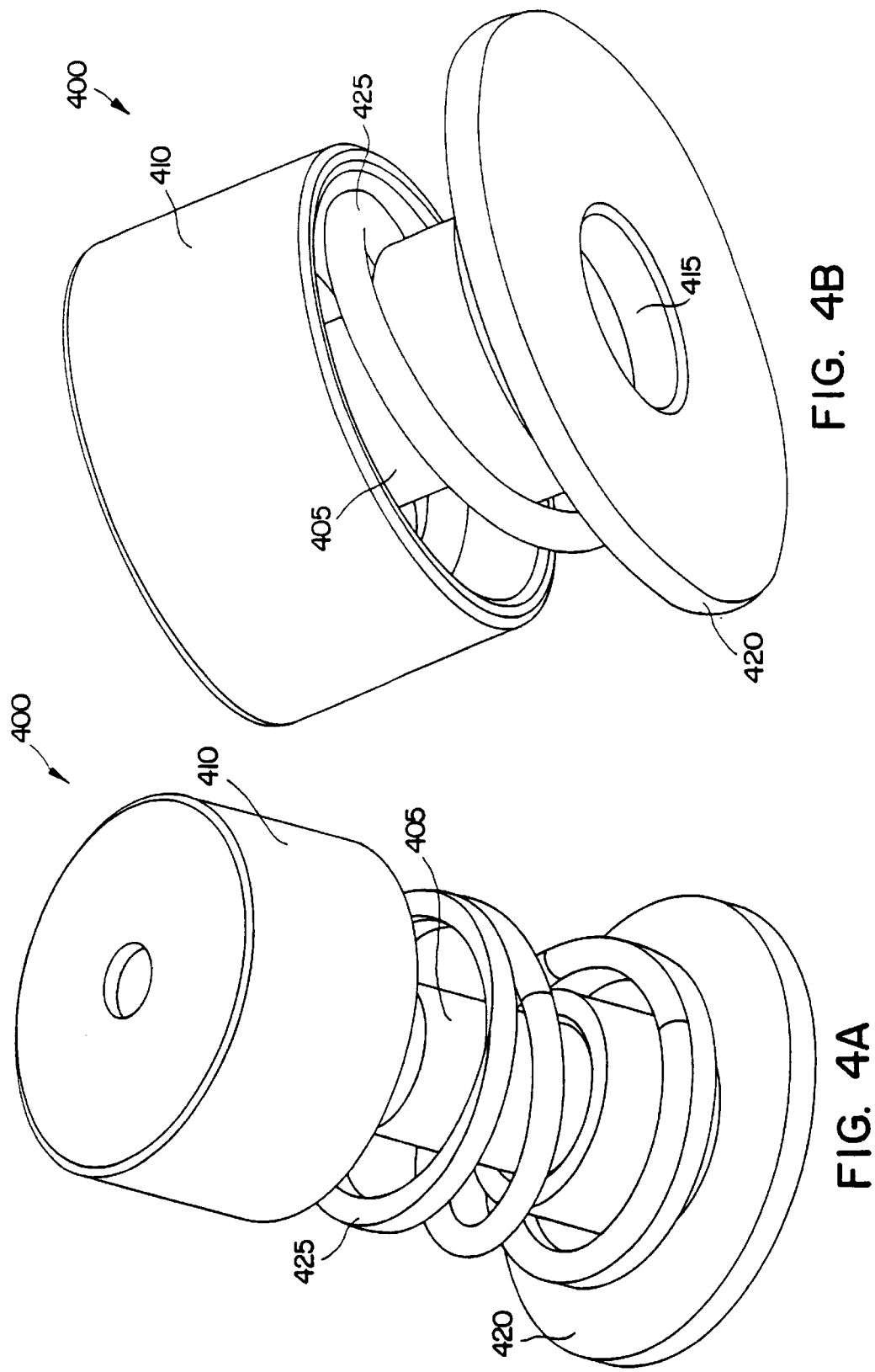

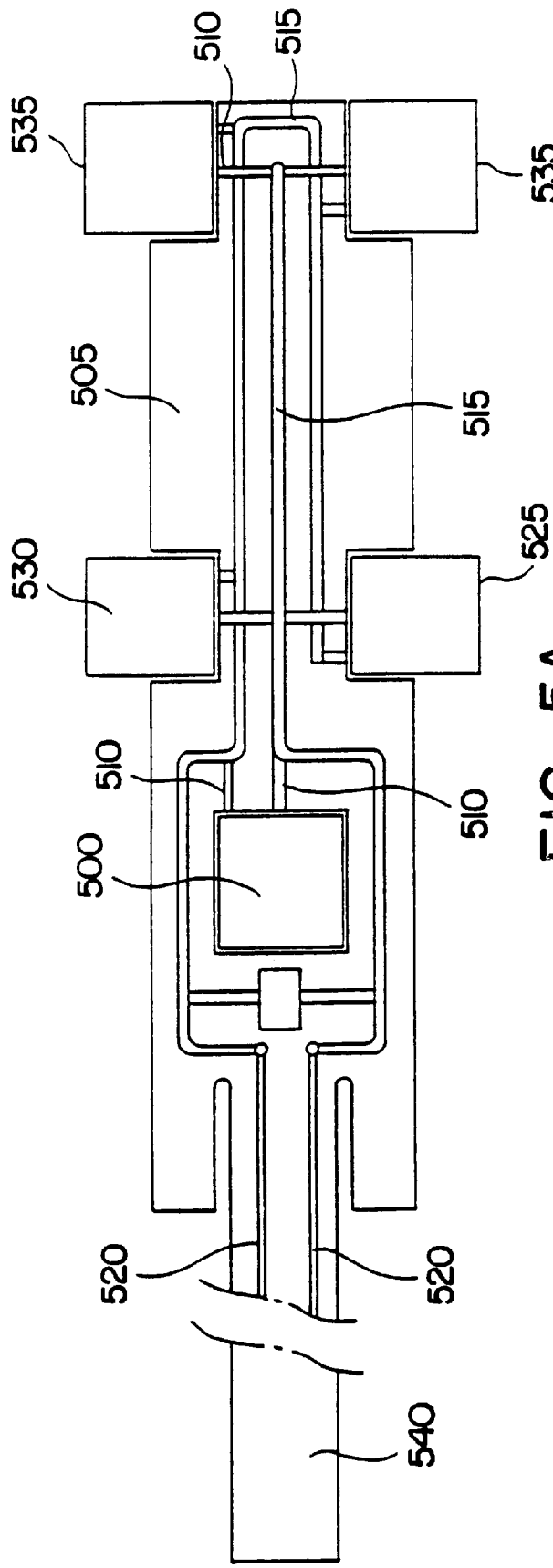
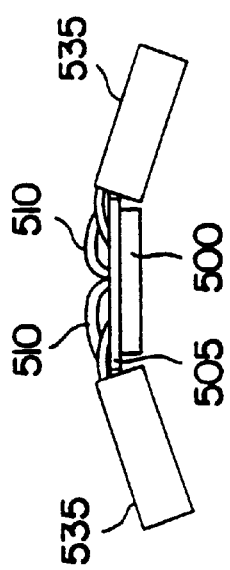
FIG. 5A
FIG. 5B

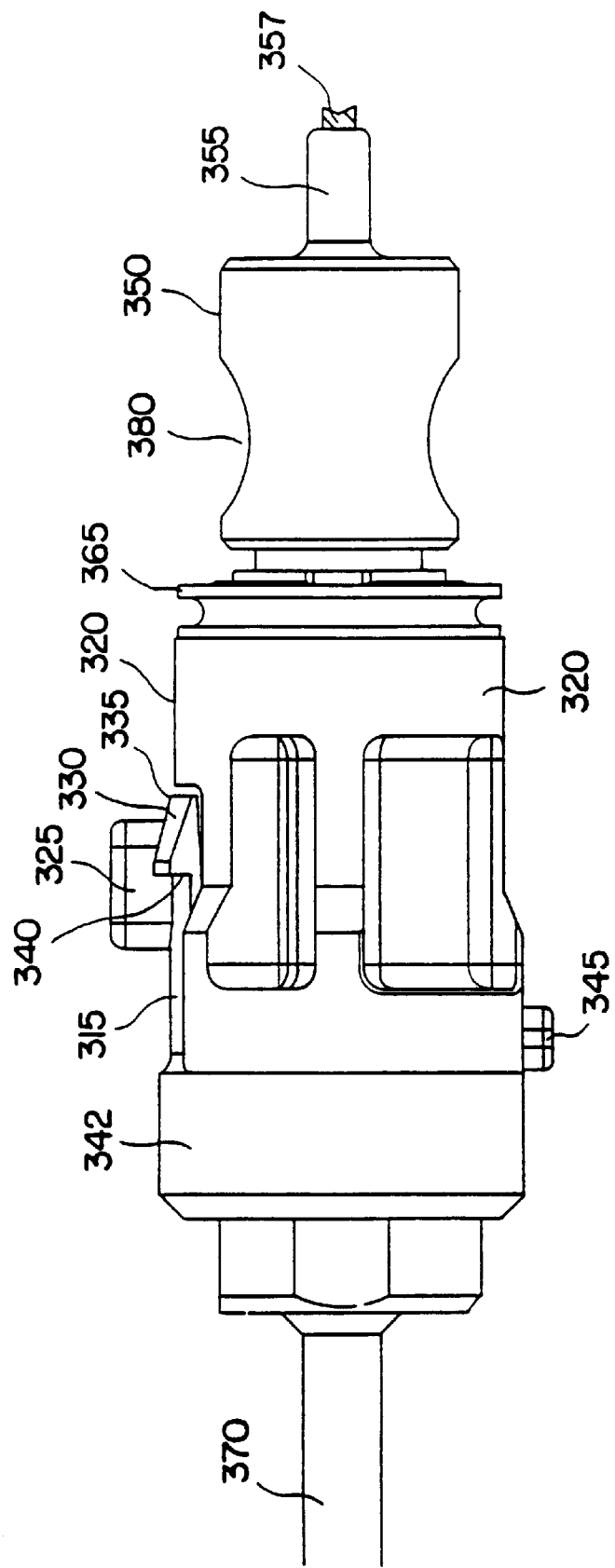

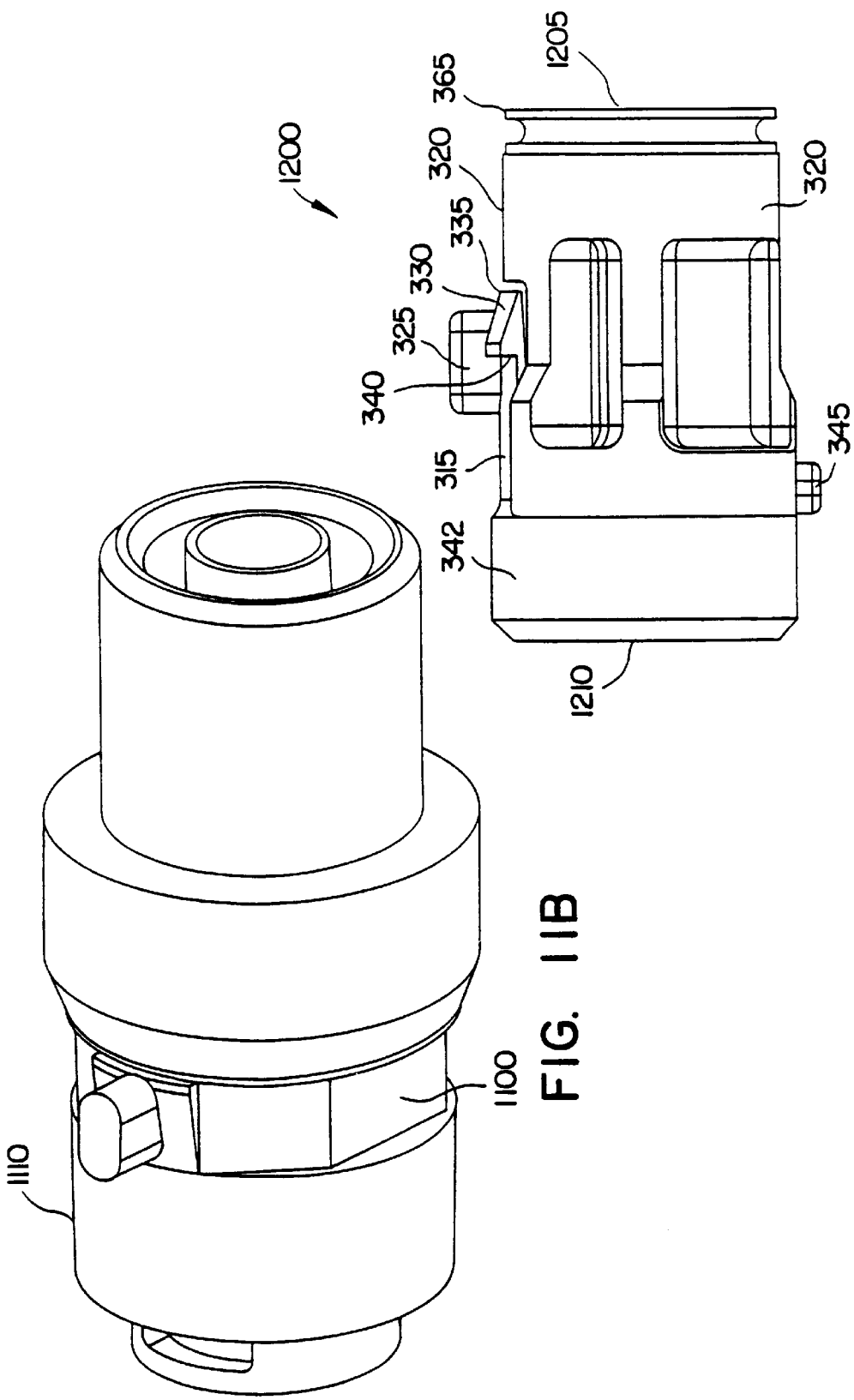

SURGICAL INSTRUMENT HANDPIECE AND SYSTEM

CROSS REFERENCE TO RELATED APPLICATIONS

This Application is a continuation of Ser. No. 08/630,537 filed Apr. 10, 1996 now U.S. Pat. No. 5,871,493, this application claims priority from U.S. Provisional Application Serial No. 60/007,117, entitled "Surgical Instrument Handpiece and System" and filed Oct. 31, 1995, which is incorporated by reference.

BACKGROUND OF THE INVENTION

A surgical system may include a motorized handpiece in which may be inserted a variety of surgical devices having different functions and operating parameters. Typically, a surgical device is engaged in a bore of a handpiece by interaction of spring-loaded ball locks in the bore with a groove around a circumference of the surgical device. Typically, the ball locks are retracted by manipulating a collar around the exterior of the handpiece to permit insertion or removal of the surgical device.

Adapters may also be employed to permit surgical devices that are not configured for use with a particular handpiece to be used with that handpiece. For example, Sjostrom, U.S. Pat. No. 4,705,038, describes a motorized handpiece that operates a set of different surgical devices. Sjostrom's system includes adapters that permit surgical devices having differently sized hubs to be used in conjunction with a single handpiece. Each adapter includes a first end configured for engagement with the handpiece and a second end configured for engagement with one or more surgical devices.

SUMMARY OF THE INVENTION

In one aspect, generally, the invention features an apparatus that includes a body configured for insertion into a bore of a surgical handpiece and a latch. The latch includes a resilient member connected to the body and having a latching structure configured to latchingly engage a surface of the surgical handpiece within the bore.

The invention provides considered advantages over the prior art. In particular, the body of the apparatus may be engaged with and released from the surgical handpiece without manipulating the handpiece. As a result, the handpiece does not need to include any moving parts for engagement with surgical devices or other instruments.

Embodiments may include one or more of the following features. The resilient member may be a cantilevered arm and may be configured to radially deflect during insertion into the bore of the handpiece and to return from the radial deflection to permit the latching structure to latchingly engage the surface of the surgical handpiece within the bore. The latch may also include a user-manipulable release portion mounted on the cantilevered arm, and the cantilevered arm may be configured to radially deflect in response to pressure on the release portion to disengage the latching structure from the surface of the surgical handpiece within the bore. This permits the apparatus to be released from the surgical handpiece with little effort. The latching structure may be positioned adjacent to the release portion or may be spaced from the release portion along a longitudinal axis of the body.

The body includes a proximal end for insertion into the bore. The latching structure may include a leading edge that is ramped in a direction from the proximal end of the body toward a distal end of the body and a latching surface oriented transversely to a longitudinal axis of the body. The latching surface may also include a trailing edge at a distal end of the latching structure. This trailing edge may be angled toward the distal end of the body in a radial direction from the body.

The body may also include a tab that extends radially from an exterior surface of the body and is positioned to engage an opening in the handpiece. The tab is positioned distally of the release portion. The body may be formed from a single piece of injection molded plastic, and may include a ring structure that carries the cantilevered arm and is secured to the body so that the arm extends proximally to and adjacent to an exterior surface of the body. The ring structure may be joined to a distal end of the body by a snap fit.

The body may be configured as a hub of a surgical instrument. When the body is configured as a hub, the surgical instrument may also include an outer member connected to and extending from the body to a tissue receiving opening at a distal end of the outer member, an inner member positioned in the outer member and including at its distal end a surgical tool to cut tissue, and a drive shaft connected to the inner member for rotating the inner member relative to the outer member. The body may carry a magnet that is sensed when the apparatus is inserted into the bore of the surgical handpiece.

The body may also be configured as an adapter for interconnecting a hub of a surgical instrument to the handpiece. The adapter includes a proximal end for insertion into the bore of the handpiece and a distal end configured for attachment to the hub of the surgical instrument.

The apparatus may be a component of a surgical device that also includes a handpiece. The handpiece has a bore at its distal end for insertion of the body of the apparatus and an annular flange located within the bore to latchingly engage the latching structure when the body is inserted into the bore. The annular flange may include a ramped edge at an end closest to the distal end of the handpiece and, at an end furthest from the distal end of the handpiece, an edge that is angled toward the distal end of the handpiece in a radial direction from a longitudinal axis of the bore (i.e., a back-cut edge). The handpiece may also include a slot and an opening at its distal end. A user-manipulable release portion of the latch is inserted into the slot when the body is inserted into the bore. A tab that extends radially from an exterior surface of the body and is positioned distally of the release portion may be inserted into the opening when the body is inserted into the bore.

In another aspect, generally, the invention features an apparatus that includes a body configured for insertion into a bore of a surgical handpiece, a latch and a tab. The latch includes a resilient member connected to the body and having a latching structure configured to latchingly engage a surface of the surgical handpiece within the bore. The latch also includes a user-manipulable release portion mounted on the resilient member. The tab extends radially from an exterior surface of the body.

Embodiments may include one or more of the features noted above.

In another aspect, generally, the invention features an apparatus that includes a body configured for insertion into a bore of a surgical handpiece and a latch that includes a resilient cantilevered arm connected to the body and having a latching structure configured to latchingly engage a surface of the surgical handpiece within the bore and a user-manipulable release portion mounted on the cantilevered arm. The resilient cantilevered arm is configured to radially deflect during insertion into the bore of the handpiece and to return from the radial deflection to permit the latching structure to latchingly engage the surface of the surgical handpiece within the bore, and to radially deflect in response to pressure on the release portion so as to disengage the latching structure from the surface of the surgical handpiece within the bore.

Embodiments may include one or more of the features noted above.

In another aspect, generally, the invention features a surgical device that includes a handpiece having a bore at its distal end and an apparatus that includes a body configured for insertion into the bore of the handpiece. The apparatus also includes a latch having a resilient member connected to the body and having a latching structure configured to latchingly engage a surface of the handpiece within the bore.

Additional embodiments may include one or more of the following features. When the apparatus is configured as a surgical instrument having a drive shaft, the drive shaft may have an extension that includes a drill tip configuration with sloped, canted edges at a proximal end of the drill tip configuration for engagement with the drive shaft of the motor.

In yet another aspect, generally, the invention features a surgical device that includes a handpiece having at its distal end a bore, a recessed portion on the exterior surface that includes a slot, an annular flange located within the bore, and an opening. The surgical device also includes a surgical instrument that has a body configured for insertion into the bore, a latching mechanism attached to the body and configured to latchingly engage with the annular flange to secure the surgical instrument to the handpiece in an axial direction, and a tab configured to engage with the opening to secure the surgical instrument to the handpiece in a circumferential direction.

Additional embodiments may include one or more of the following features. The annular flange may be positioned proximally of a proximal end of the slot of the recessed portion. The latching mechanism may include a latch and a user-manipulable release portion configured to move the latch from an engaging position in which the latch engages the annular flange to a non-engaging position in which the latch is disengaged from the annular flange when the release portion is depressed. The latching mechanism may also include a cantilevered arm that is radially spaced from an exterior surface of the body, and on which the user-manipulable release portion is mounted. A spring-loaded plunger may be coupled between the latch and the user-manipulable release portion. In addition, the slot of the recessed portion may have a flared opening at its distal end.

In yet another aspect, generally, the invention features a surgical handpiece having a proximal end and a distal end. At its distal end, the handpiece includes a bore configured for reception of a body of a surgical apparatus, a recessed portion on the exterior surface that includes a slot for reception of a user-manipulable release button of the surgical apparatus, an annular flange located within the bore and configured to latchingly engage with a latching structure of the surgical apparatus to secure the surgical apparatus within the bore in a direction corresponding to a longitudinal axis of the bore, and an opening configured to engage a tab of the surgical apparatus to secure the surgical apparatus within the bore in a circumferential direction.

Additional embodiments may include one or more of the following features. The annular flange may be located at a position in the bore corresponding to the slot of the recessed portion and may include a gap corresponding to the slot. Alternatively, the annular flange may be located at a position in the bore that is proximal to the slot of the recessed portion.

In yet another aspect, generally, the invention features a surgical instrument that includes a body configured for insertion into a bore of a handpiece, a latching mechanism and a tab. The latching mechanism includes a latch and a user-manipulable release portion. The release portion is configured to move the latch radially between a first position in which the latch engages a surface within the bore of the handpiece and a second position in which the latch is disengaged from a surface within the bore of the handpiece when the release button is depressed. The tab extends radially from an exterior surface of the body and is positioned distally of a release portion of the latching mechanism.

Embodiments may include one or more of the features noted above.

In yet another aspect, generally, the invention features a surgical instrument that includes a body disposed along an axis. The body is configured to be received in a bore of a surgical handpiece. At least a portion of the body includes a ramped leading surface configured to be advanced past a latching surface within the bore while the body is being inserted into the bore, and an engagement surface oriented transversely with respect to the axis of the body and configured to engage the latching surface when the body is fully inserted into the bore. The surgical instrument also includes a release mechanism for disengaging the engagement surface from the latching surface to allow the body to be withdrawn from the bore.

Embodiments may include one or more of the features noted above.

Other features and advantages will become apparent from the following description of the preferred embodiments, including the drawings, and from the claims.

BRIEF DESCRIPTION OF THE DRAWINGS

FIG. 3A is a side cross sectional view of a surgical handpiece.

FIG. 3B is an enlarged portion of the cross sectional view of FIG. 3A.

FIG. 4A is an exploded top perspective view of a magnetic switching element of the handpiece of FIG. 1.

FIG. 4B is a bottom perspective view of the magnetic switching element of FIG. 4A.

FIG. 5A is a top view of a circuit board of the handpiece of FIG. 1.

FIG. 5B is an end view of the circuit board of FIG. 5A.

FIG. 6C is a side view of the hub and drive shaft of FIG. 6B.

FIGS. 11A and 11B are perspective views of an alternative latching mechanism.

FIG. 12 is a side view of an adapter including the latching mechanism of FIGS. 6A–6C.

DESCRIPTION OF THE PREFERRED EMBODIMENTS

Figure 1:
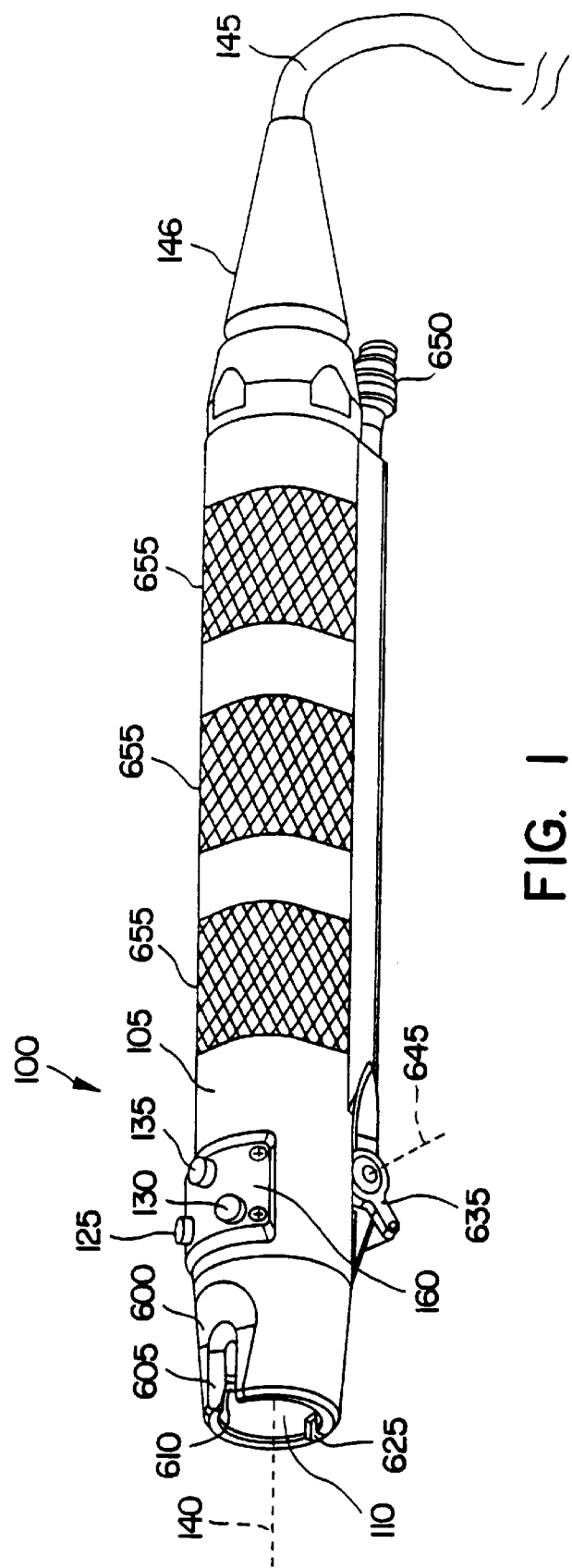
FIG. 1 is a perspective view of a surgical handpiece.
Figure 2:
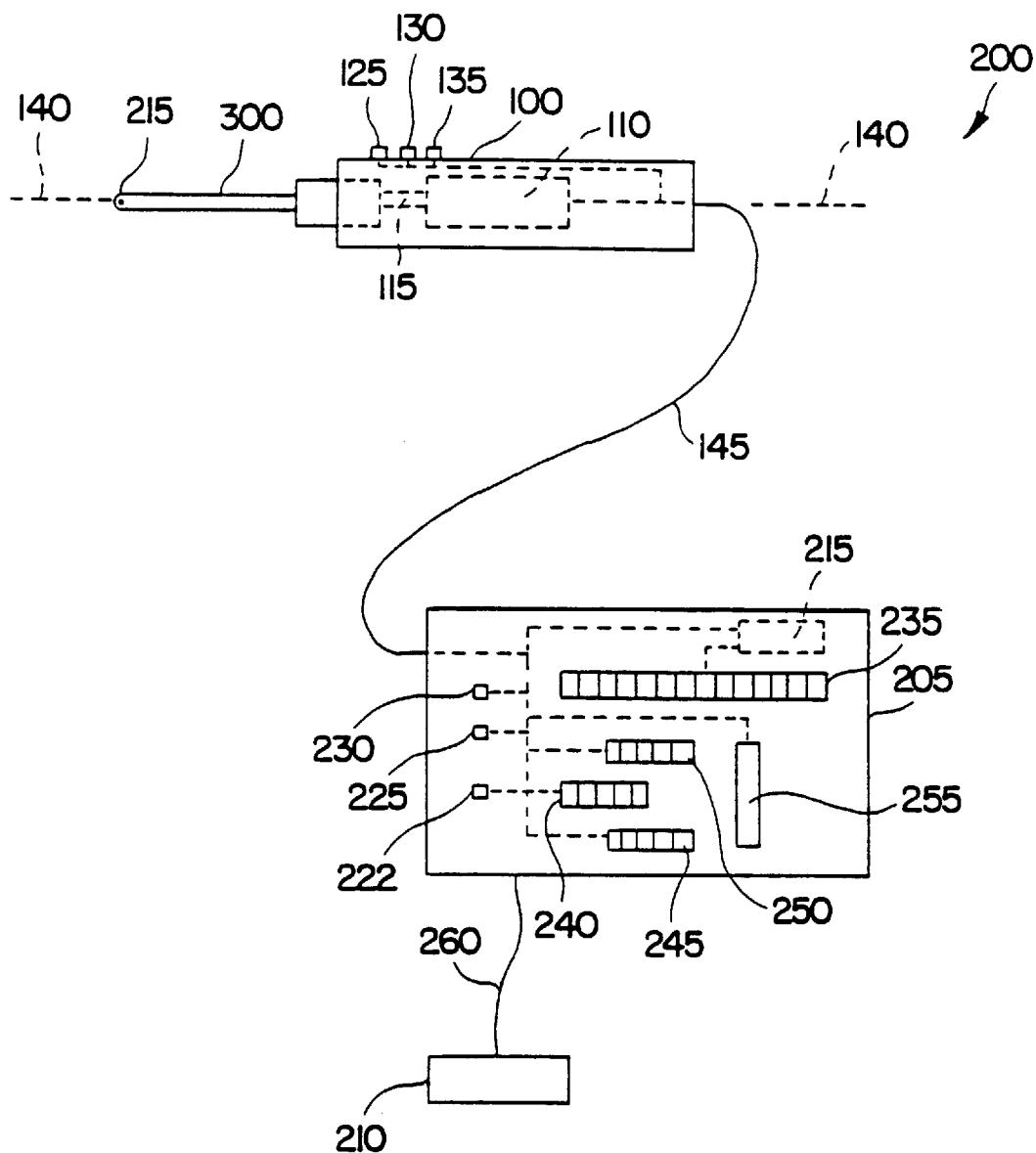
FIG. 2 is a block diagram of a surgical system including the handpiece of FIG. 1.

With reference to FIGS. 1 and 2, a motorized, reusable surgical handpiece 100 (FIG. 1) is configured to operate a variety of disposable (or reusable) surgical instruments. The handpiece has a generally cylindrical shape, with a teardrop-shaped cross section, and includes a housing 105 made from a non-magnetic material such as aluminum. At its distal end, the handpiece includes a cylindrical bore 110 for attachment of a surgical instrument. Within the bore 110 is a drive shaft 115 that is coupled to a motor 120 positioned within the handpiece 100. The handpiece includes pushbutton switches 125, 130 and 135 that produce signals for use in controlling the motor 120. The handpiece 100, including the pushbutton switches 125, 130 and 135, is fully autoclavable. The design of the handpiece is further illustrated in U.S. Design Application Ser. No. 29/045,831, entitled "Surgical Handpiece" and filed Oct. 31, 1995, which is incorporated by reference.

The handpiece 100 is employed in a surgical system 200 that includes the handpiece, a console 205, a surgical instrument 300 (or a set of surgical instruments), and a foot control assembly 210. A processor 215 positioned within the console 205 controls the operating speed and direction of the motor 120 of the handpiece 100. This, in turn, controls the operating speed and direction of the surgical instrument 300. For example, when the surgical instrument 300 includes an active portion 305 (such as a cutting blade or an abrading burr) that rotates about the longitudinal axis 140 of the handpiece 100, the processor 215 controls the direction and speed at which the active portion 305 rotates.

The processor 215 controls the motor 120 in response to signals from the pushbutton switches 125, 130 and 135, the console 205, and the foot control assembly 210. In addition, as discussed below, the handpiece 100 provides the processor 215 with information indicative of the instrument type of the surgical instrument positioned in the handpiece. The handpiece 100 is connected to the console 205 by a cable 145 that is attached to the proximal end of the handpiece by a threaded connector 146.

In addition to the processor 215, the console 205 includes a power switch 220 for activating or deactivating the system, and buttons to increase (225) or decrease (230) the speed of the handpiece motor 120. To display information, the console includes a sixteen character fluorescent display 235 for diagnostic messages, digital displays of the motor speed (240) and the permissible range for the motor speed (245, 250), and a bar graph display 255 of the motor speed within the permissible range. The foot control assembly 210 is attached to the console 205 through a cable 260 and permits an operator to select between forward, reverse and oscillate modes of operation for the motor 120 of the handpiece 100. Alternatively, the foot control assembly can be used to control the position of an operative portion of the surgical instrument. Systems for such position control are discussed in U.S. application Ser. No. 08/420,243, entitled "Motor Controlled Surgical System and Method Having Positional Control", which was filed on Apr. 11, 1995 and U.S. application Ser. No. 08/529,191, entitled "Method and Apparatus for Automatically Controlling and Scaling Motor Velocity", which was filed on Sep. 15, 1995, both of which are incorporated by reference.

Referring also to FIGS. 3A and 3B, the three pushbutton switches 125, 130 and 135 are attached to the exterior of the housing 105 and are physically isolated from the electronic circuitry associated with the switches by a wall of the housing. This isolation ensures that the switches do not provide a leakage path to the electronics and thereby ensures that the handpiece 100 and the switches 125, 130 and 135 are autoclavable. In addition, no separate seal is required to isolate the switches from the circuitry. The switches, which are round and identically sized, are located near the distal end of the handpiece 100 and are arranged in a triangular configuration. Fewer or more switches (e.g., two or four switches) could be used and the switches could be arranged in a different configuration.

As already discussed, the switches 125, 130 and 135 provide signals to the processor 215 through cable 145, and the processor 215 uses the control signals to control the motor 120 in the handpiece 100. The functions of the switches need not be explicitly defined and may be configured by programming the processor 215. For example, switch 125 may cause the processor 215 to control the motor 120 to cycle through forward, reverse and oscillate modes of operation, while switch 130 causes the processor to cycle the motor through a circular range of speeds and switch 135 causes the processor to activate or deactivate the motor.

In another configuration, the switches respectively cause the processor to control the motor to operate in a forward mode (switch 125), a reverse mode (switch 130), or an oscillate mode (switch 135). In this alternative configuration, pressing any one of the switches activates the motor and causes the motor to operate in the corresponding mode. Thereafter, pressing any switch deactivates the motor. To switch, for example, from the forward operating mode to the reverse operating mode, an operator would press any one of the three switches to deactivate the motor and would thereafter press switch 130 to reactivate the motor in the reverse mode.

Each of switches 125, 130 and 135 also may have multiple functions. For example, quickly pressing a switch may cause the motor to switch between forward and reverse modes of operation while continually pressing the switch causes the motor to operate in an oscillation mode. Similarly, quickly pressing a switch may activate the motor while continually pressing the switch gradually increases the speed of the motor or controls the position of an operative portion of the surgical instrument as discussed above.

Referring also to FIGS. 4A and 4B, each of switches 125, 130 and 135 comprises a magnetic switching element 400 that includes a permanent magnet 405 surrounded by magnetically soft material. The magnetically soft material absorbs the magnetic field produced by magnet 405 to shunt the magnet to prevent the magnetic field from actuating switching circuitry in the handpiece until the switch is depressed by the user, and do so without becoming magnetized over time.

Figure 4C:
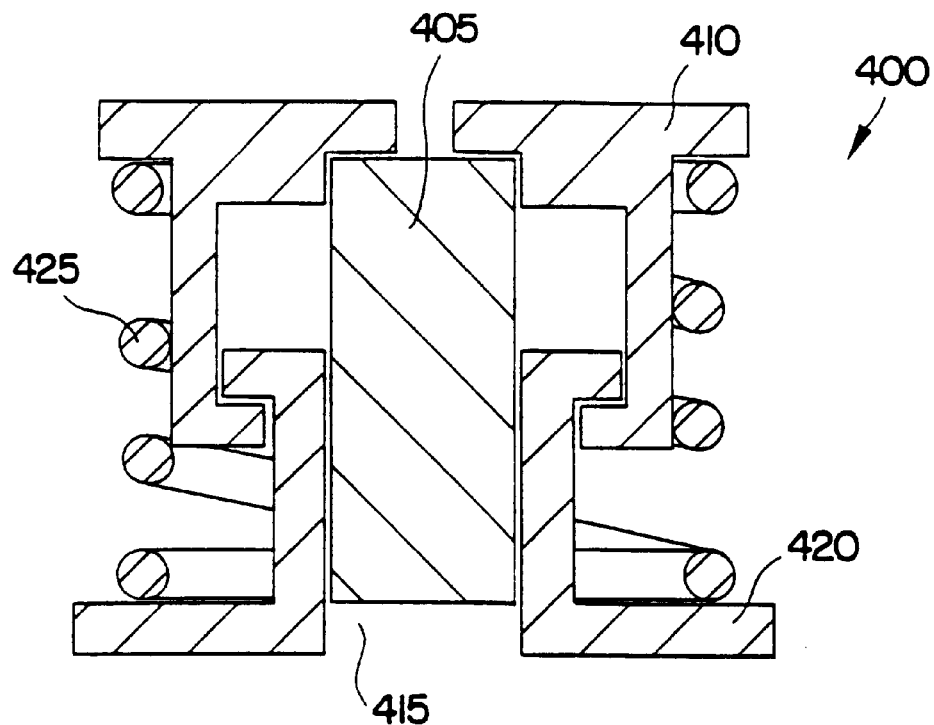
FIG. 4C is a cross sectional view of an alternative magnetic switching element.

Each of switches 125, 130 and 135 includes a rubber boot 150 positioned over the magnetic switching element 400. The rubber boots 150 are formed in a sheet of silicone rubber 155 that is secured to the housing 105 of handpiece 100 by a metal cover 160. The permanent magnet 405 of each magnetic switching element 400 is secured to a switch cover 410 and positioned within a cylindrical opening 415 of a switch bottom 420. The switch cover 410 serves as an actuator for the switch. A spring 425 biases the switch cover 410 away from the switch bottom 420, and rubber boot 150 maintains the switching element 400 as a single unit. In an alternative arrangement, as illustrated in FIG. 4C, switch cover 410 and switch bottom 420 are mechanically interlocked so that rubber boot 150 serves no role in maintaining switching element 400 as a single unit. The switch cover 410, switch bottom 420 and spring 425 are made from a magnetically soft material such as Carpenter 430F solenoid quality magnetically soft stainless steel. Other magnetically soft materials such as magnetically soft iron could also be used, but magnetically soft stainless steel is employed for its corrosion resistance.

The magnetic switching elements 400 are positioned and configured to interact with corresponding Hall-effect sensors that are physically isolated from the switching elements. Each magnetic switching element 400 is positioned in a recessed portion 165 of the housing 105. In particular, each magnetic switching element 400 is positioned on a recessed shelf 170 that is sized to accommodate the switch bottom 420 and overlies a depression 175 in the housing. The depression 175 has a diameter that is slightly larger than the diameter of the cylindrical opening 415 of the switch bottom 420 and has a closed bottom. For example, at the bottom of the depression 175 corresponding to switch 135 is a wall 180 of the housing 105 that physically isolates the magnetic switching element 400 from a Hall-effect sensor 500 that corresponds to the switch 135. This physical isolation provides a barrier against any potential leakage path through the switch 135. However, because the housing 105 is made from aluminum, a non-magnetic material, the magnetic switching element 400 is not magnetically isolated from the Hall-effect sensor 500.

When switch 135 is not depressed, the permanent magnet 405 is positioned within a volume defined by the switch cover 410 and switch bottom 420. As noted above, these elements absorb the magnetic field produced by the permanent magnet 405. When the permanent magnet 405 is positioned within the volume defined by the switch cover 410 and the switch bottom 420, these elements, along with the spring 425, complete a magnetic circuit that prevents a significant portion (if not all) of the magnetic field produced by the permanent magnet 405 from reaching the Hall-effect sensor 500. That is, the magnetic field is decoupled from the Hall-effect sensor 500.

Figure 4D:
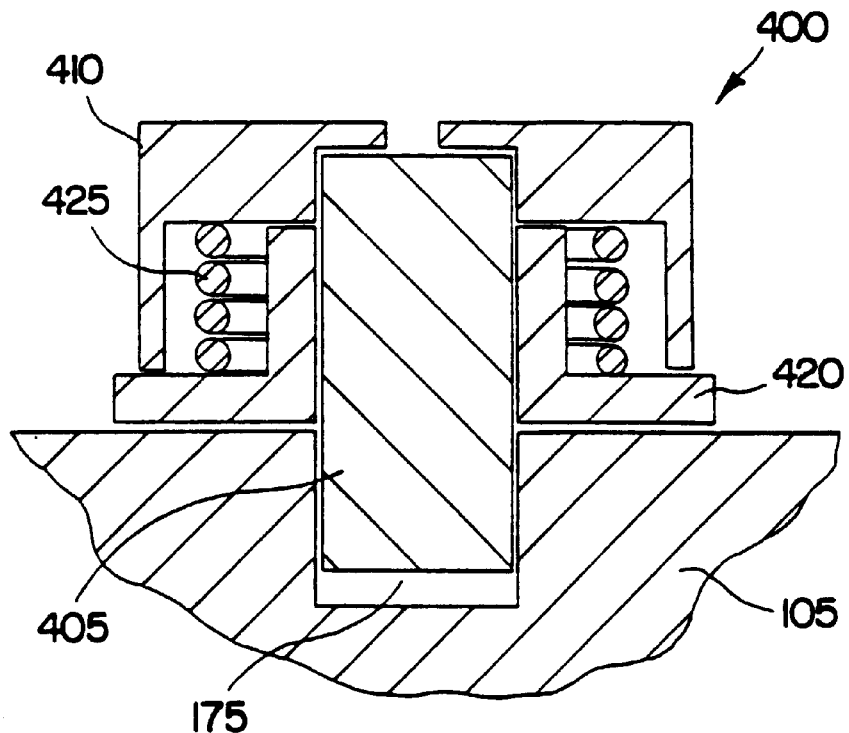
FIG. 4D is a cross sectional view of the magnetic switching element of FIG. 4A in a depressed position.

As illustrated in FIG. 4D, depressing switch 135 causes a portion of the magnet 405 to extend beyond switch bottom 420 into the depression 175. As noted above, the housing 105 of the handpiece 100 is made from aluminum, a material that does not absorb the magnetic field and does not shunt the magnet 405. Thus, depressing switch 135 causes a portion of the magnet 405 to move from a shunted position to a relatively unshunted position. When the magnet 405 is in the unshunted position, the magnetic field produced by magnet 405 is coupled to and sensed by the Hall-effect sensor 500. Similar results could be obtained if the housing 105 were made from another non-magnetic material such as plastic or austenitic non-magnetic stainless steel.

The Hall-effect sensor 500 responds to the magnetic field by sending a signal to console 205 along a multiplexed bus in cable 110. The Hall-effect sensor 500 is a model A3054SU Hall-effect sensor supplied by Allegro Microsystems, Inc. of Worcester, Mass. The sensor includes a high-resolution bipolar Hall-effect switching circuit that drives high-density CMOS logic stages. The logic stages decode serial address pulses sent by processor 215 on the multiplexed bus and produce a response when an appropriate address is received. This response is indicative of whether the Hall-effect sensor has detected a magnetic field. Processor 215 responds to the signal from the Hall-effect sensor 500 by controlling the motor 120 in accordance with the function of the switch 135. Operation of the multiplexed bus is described in detail in U.S. Provisional Application Serial No. 60/007,133, entitled "Motor Controlled Surgical Instrument" and filed Oct. 31, 1995, and a U.S. utility application being filed herewith entitled "Motor Controlled Surgical Instrument" and naming Michael A. Brodsky and Kenneth W. Krause as inventors, both of which are incorporated by reference. The Allegro sensor also includes an input that permits connection of a mechanical switch. Thus, if desired, a mechanical switch could be coupled to the magnetic switching element 400 for redundancy or as a failsafe measure, or could replace the magnetic switching element 400. However, such an arrangement would likely require the formation of a physical passage through the housing 105. Other magnetic sensors such as, for example, Hall-effect sensors by other manufacturers or reed switches, could also be used.

Switch 135 has a stroke length on the order of 0.06 inches (i.e., the magnet 405 is 0.06 closer to the Hall-effect sensor 500 when switch 135 is depressed than it is when switch 135 is not depressed). Thus, the physical distance between the magnet 405 and the Hall-effect sensor 500 is of little significance to whether the Hall-effect sensor 500 detects the magnetic field produced by the magnet 405. Rather, the significant factor is whether magnet 405 is extended beyond switch bottom 420 so that the magnet 405 is no longer shunted and the magnetic field is permitted to reach the Hall-effect sensor 500. Magnet 405 is shunted during the first third of the stroke of switch 135, and is extended beyond switch bottom 420 during the second two thirds of the stroke.

Referring also to FIGS. 5A and 5B, Hall-effect sensor 500 is mounted on a circuit board 505 that is positioned in a channel 185 in the housing of the handpiece 100. The circuit board 505 is flat, 15 mils thick, and only slightly flexible. Hall-effect sensor 500 is positioned within a cutout in the circuit board 505, and is connected to the circuit board by leads 510 that are soldered to a pair of circuit paths 515 that define the bus which electrically connects the Hall-effect sensor 500 to the console 205. Wires 520 connected to the circuit paths 515 transmit signals to and from the console 205.

Hall-effect sensors 525 and 530, which correspond, respectively, to switches 125 and 130, are positioned in cutouts in the side of circuit board 505 and located beneath switches 125 and 130. Sensors 525, 530 are angled relative to the circuit board 505 to accommodate curvature of the handpiece 100, and are connected by leads 510 that are soldered to the circuit paths 515.

An additional pair of Hall-effect sensors 535 are positioned adjacent to the bore 110 and respond to magnets in the surgical instruments to identify the type of instrument installed in the handpiece 100. Sensors 535 are angled and connected in the same way as are sensors 525 and 530. The Hall-effect sensors 535 detect whether magnets are present in each of two chambers within a surgical instrument and provide this information to the processor 215. Using this information, the processor 215 identifies an instrument type to which the instrument belongs and uses the instrument type to carry out subsequent processing. For example, the processor 215 may use the instrument type to set the permissible range of operating speeds for the instrument. Through use of the two Hall-effect sensors 535, up to four different instrument types (i.e., no magnets, a magnet in one of the chambers, a magnet in the other chamber, magnets in both chambers) may be encoded. Additional Hall-effect sensors 535 and corresponding magnet chambers could be employed to encode larger numbers of instrument types (e.g., four Hall-effect sensors 535 could encode 16 instrument types). Techniques for encoding instrument types are described in U.S. Pat. Nos. 4,705,038 and Re. 34,556, which are entitled "Surgical System for Powered Instrument" and are incorporated by reference.

The circuit board 505 also includes an extension 540 that aids in insertion of the circuit board 505 into the channel 185.

Figure 6A:
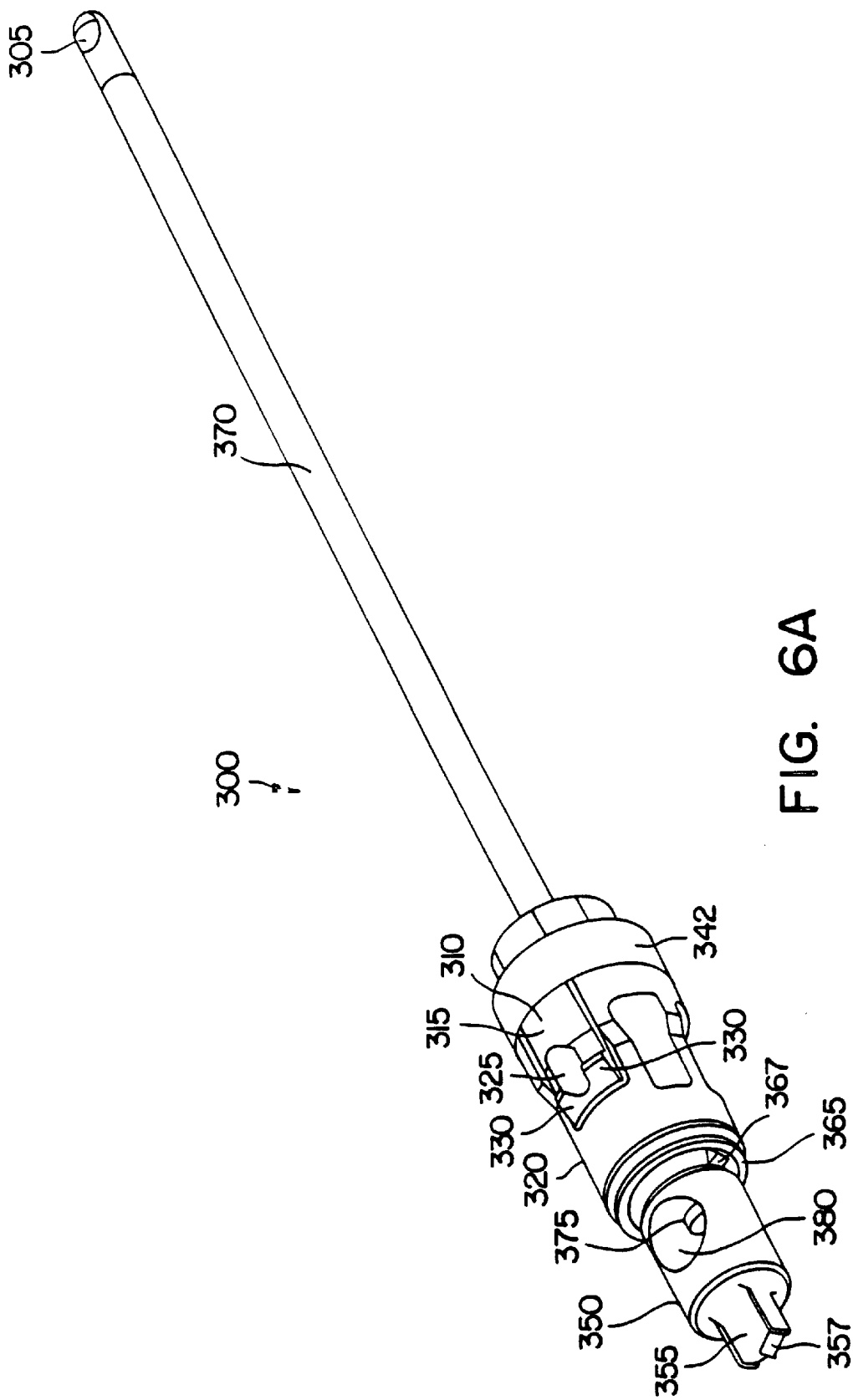
FIG. 6A is a perspective view of a surgical instrument configured for attachment to the handpiece of FIG. 1.
Figure 6B:
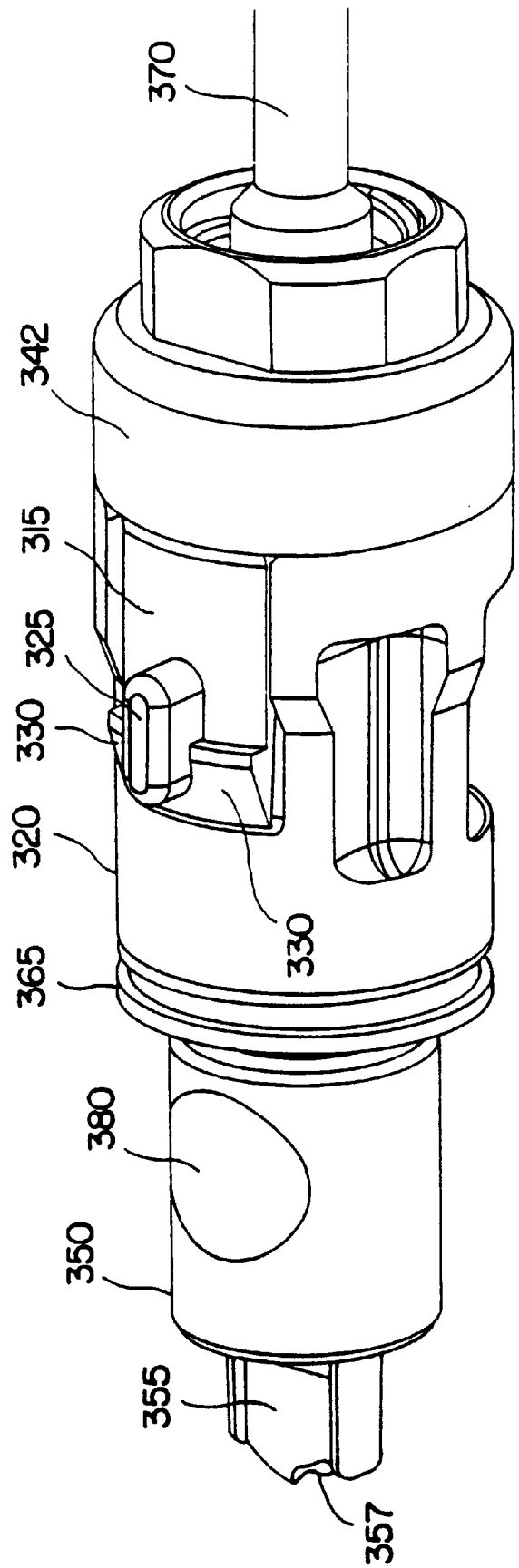
FIG. 6B is a perspective view of a hub and drive shaft of the surgical instrument of FIG. 6A.
Figure 7A:
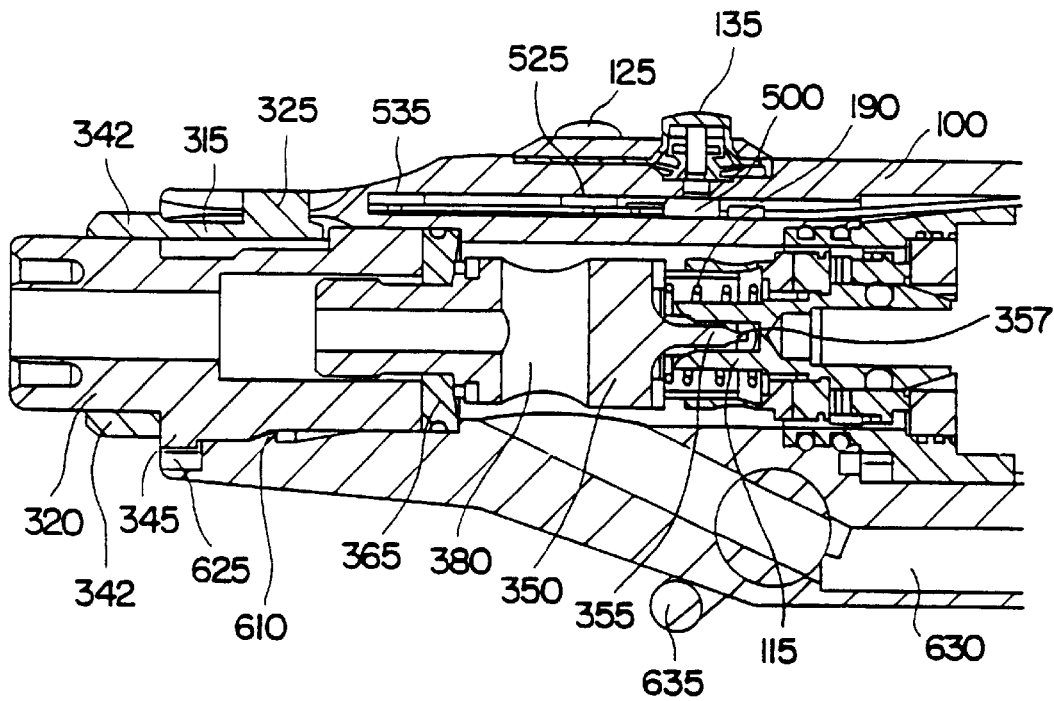
FIG. 7A is a cross sectional side view of an interface between the handpiece of FIG. 1 and the hub and drive shaft of FIGS. 6A–6C, taken at the longitudinal axis of the handpiece.
Figure 7B:
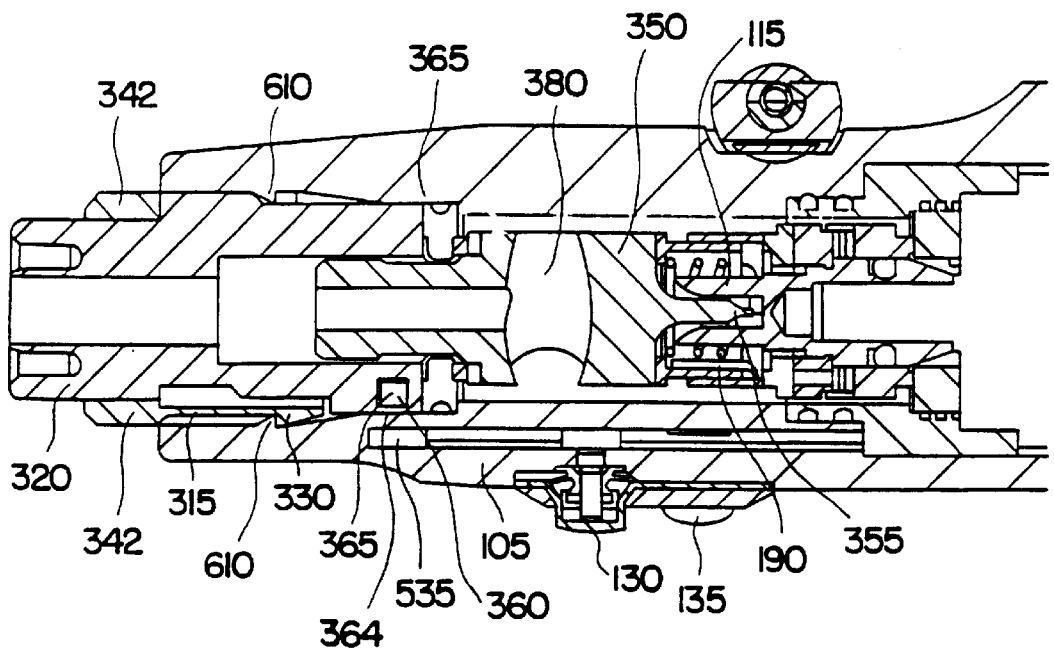
FIG. 7B is a cross sectional side view of the interface of FIG. 7A, offset from the longitudinal axis of the handpiece.

Referring to FIGS. 6A–6C, a disposable surgical instrument 300 for use with the surgical handpiece discussed above includes a resilient latching mechanism 310 and is configured for insertion into the handpiece 100 without manipulating the latching mechanism 310 or any latching mechanism on the handpiece. The latching mechanism 310 includes a cantilevered resilient arm 315 that is radially spaced from an exterior surface of a hub 320 of the instrument 300. A user-manipulable release button 325 is mounted on the cantilevered arm with ramped latches 330 positioned on either side of the release button 325. Each of the latches 330 includes a ramped leading edge 335 and a back-cut trailing edge 340. The design of the surgical instrument is further illustrated in U.S. Design Application Ser. No. 29/045,832, entitled "Hub for a Surgical Instrument" and filed Oct. 31, 1995, which is incorporated by reference.

The hub 320 is formed from a single piece of injection molded plastic to which is secured a ring structure 342 that carries cantilevered arm 315 so that arm 315 extends proximally and adjacent to the exterior surface of hub 320. The ring structure 342 is joined to the distal end of the hub 320 by a snap fit. In alternative arrangements, the ring structure could be integral to the hub or secured to the proximal end of the hub. When the ring structure is secured to the proximal end of the hub, the orientation of the latches 330 relative to the resilient arm 315 are reversed so that the latches 330 continue to have ramped leading edges and back-cut trailing edges.

Referring also to FIGS. 1, 3A, 7A and 7B, the bore 110 of the handpiece 100 is configured to engage with the latching mechanism 310 of the surgical instrument 300. For this purpose, the exterior surface of the distal end of the handpiece includes a recessed portion 600 having a slot 605 for insertion of the release button 325 of the surgical instrument when the hub 320 is inserted into the bore 110. The recessed portion is provided for ease of operation and helps to eliminate any chance that a surgical instrument positioned in the handpiece will be inadvertently released.

An annular flange 610 within the bore 110 engages the ramped latches 330 of the surgical instrument to axially secure the instrument to the handpiece 100. The annular flange 610 has a ramp-shaped leading edge 615 and a back-cut trailing edge 620. With the exception of the region defined by the slot 605, the annular flange extends around the entire interior diameter of the bore 110. However, a partial flange could also be used. Indeed, the only functional limitation on the flange is that it engage the latching mechanism 310. As such, the annular flange 610 need not include a ramp-shaped leading edge or a back-cut trailing edge and could have, for example, a square or rectangular cross section. In addition, should excessive wear be a concern, the annular flange 108 could be formed with a steel insert.

A guide slot 625 interacts with a tab 345 that protrudes from surgical instrument hub 320 to radially secure the surgical instrument to the handpiece and prevent rotation of the surgical instrument in response to torque applied by the motor 120. As illustrated, the guide slot 625 only extends through a portion of the radial dimension of the handpiece and is configured to accept an equally sized tab. The dimensions of the guide slot and the tab may be varied to prevent the use of certain surgical instruments in conjunction with certain handpieces. For example, an alternative handpiece could include a guide slot extending completely through the radial dimension. Surgical instruments configured for use only with the alternative handpiece could include a tab that is longer in the radial direction than is the guide slot of the present handpiece so that those instruments would not be attachable to the present handpiece. This arrangement would still permit surgical instruments that are attachable to the present handpiece to be attached to the alternative handpiece.

The tab 345 is located on the hub 320 opposite the latching mechanism 310 and distally of the release button 325. Accordingly, radial alignment of the tab 345 with the guide slot 625 as the surgical instrument 300 is inserted into the handpiece 100 is ensured by alignment of the release button 325 in the slot 605.

Figure 8A:
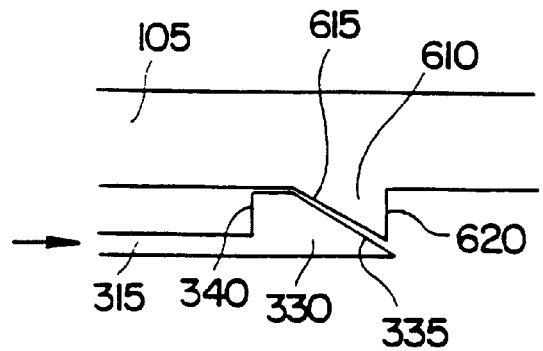
FIGS. 8A–8D are functional diagrams of the latching mechanisms of the interface of FIG. 7A.
Figure 8B:
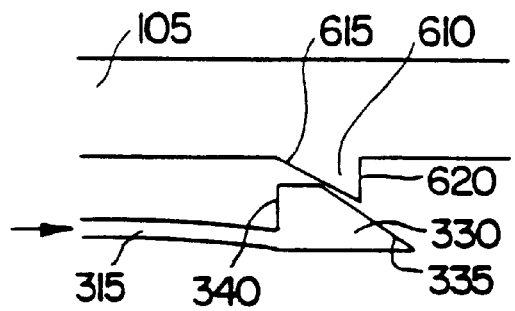
Figure 8C:
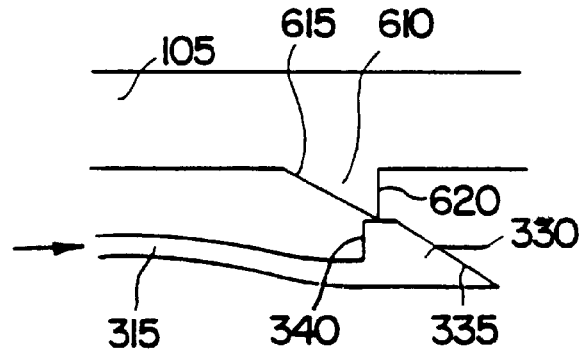
Figure 8D:
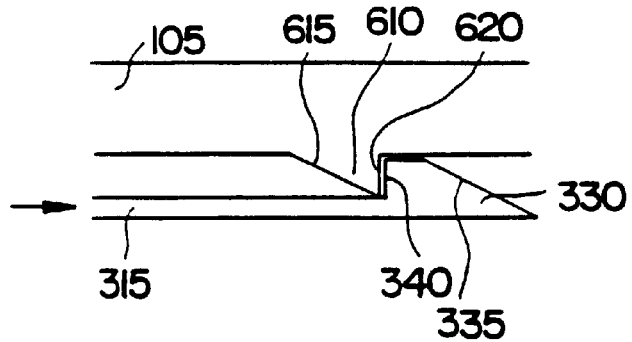

With reference also to FIGS. 8A–8D, the latching mechanism 310 of the surgical instrument 300 permits an operator to fixedly engage the surgical instrument 300 with the handpiece 100 by merely inserting the hub 320 into the bore 110 of the handpiece 100. The hub is inserted with the release button 325 aligned with the slot 605, which has a flared opening to ease alignment (FIG. 1). As the hub is inserted, the ramped leading edges 335 of the ramped latches 330 engage with the ramped leading edge 615 of the annular flange 610 (FIG. 8A). Additional insertion force causes the resilient arm 315 to bend as the ramped leading edges move past each other (FIG. 8B). Eventually, the trailing edges 340 of the ramped latches 330 pass the trailing edge 620 of the annular flange 610 (FIG. 8C). At this point, the resilient arm 315 returns to its normal, unbent orientation and the ramped latches 330 snap into place with their trailing edges against the trailing edge of the annular flange 610 (FIG. 8D). Because the trailing edges of both the annular flange 610 and the ramped latches 330 are back-cut, the hub 320 moves slightly toward the distal end of the handpiece 100 when the latches 330 snap into place.

Referring to FIGS. 6A–6C, the surgical instrument 300 includes a drive shaft 350 that is inserted into the hub 320. The drive shaft 350 includes an extension 355 that engages with the spring-loaded, sealed drive shaft 115 of the handpiece 100. When the surgical instrument 300 is positioned in the handpiece 100, rotation of the drive shaft 115 causes the drive shaft 350 to rotate. Techniques for sealing the drive shaft 115 are described in U.S. Pat. No. 5,133,729, which is entitled "Motor-Driven Hand-Piece for a Surgical Tool" and is incorporated by reference.

To ease alignment of extension 355 with drive shaft 115, extension 355 includes a drill tip configuration 357 with sloped, canted edges at its proximal end. If extension 355 is not aligned with drive shaft 115 as the surgical instrument is inserted into the handpiece, the drill tip configuration 357 engages with the drive shaft 115 and causes the extension 355 (along with the drive shaft 350) to rotate until the extension and the drive shaft are properly aligned.

The spring loading of drive shaft 115 effects a distally directed force against the hub 320 through the drive shaft 350. This force serves to secure the surgical instrument 300 in the bore 110. Additional securing force is provided by a compliant rubber seal 365 that is secured to the hub 320 by a pair of tabs 367 and provides a fluid-tight seal with the walls of the bore 110.

When the ramped latches 330 are engaged with the trailing edge of the annular flange 610, the spring 190 of the drive shaft 115 is compressed and exerts a force against the ramped latches 330 through the drive shaft 350 and the hub 320. This force secures the ramped latches 330 against the annular flange 610. Since the trailing edges of both the annular flange 610 and the ramped latches 330 are back-cut, the force exerted by the spring 190 must be overcome before the latches 300 can be disengaged from the flange 610.

In addition to providing ease of engagement between the handpiece 100 and the surgical instrument 300, the latching mechanism 310 permits the operator to release the instrument 300 from the handpiece 100 by simply pressing release button 325, and does not require manipulation of the handpiece 100 or further manipulation of the surgical instrument 300. When the release button 325 is pressed, the trailing edges of sloped ramps 330 are moved along the trailing edge of the annular flange 610 until the trailing edges no longer contact the annular flange (FIG. 8C). At that point, the spring 190 of the drive shaft 115 forces the surgical instrument 300 away from the proximal end of the handpiece 100 until the spring 190 is no longer compressed.

The hub includes a pair of radially extending chambers 360 (FIG. 7B) in which may be embedded magnets 362. As discussed above, the magnets 365 interact with Hall-effect devices 535 to identify the instrument type of surgical instrument 300. Each chamber 360 is covered by a plastic cap 364. Techniques for embedding the magnets are described in application Ser. No. 08/538,298, entitled "Surgical Instrument with Embedded Coding Element" and filed on Oct. 2, 1995, which is incorporated by reference.

Surgical instruments may be configured to perform a variety of surgical operations. Numerous examples of surgical instruments are provided in, for example, U.S. Pat. No. 4,203,444, entitled "Surgical Instrument Suited for Closed Surgery"; U.S. Pat. No. 4,274,414, entitled "Meniscal Cutter (Surgical Instrument)"; U.S. Pat. No. 4,522,206, entitled "Surgical Instrument"; U.S. Pat. No. 4,662,371, entitled "Surgical Instrument"; U.S. Pat. No. 4,834,729, entitled "Arthroscopic Surgical Instrument"; U.S. Pat. No. 4,842,578, entitled "Surgical Instrument for Arthroscopic Arthroplasty"; U.S. Pat. No. 4,983,179, entitled "Arthroscopic Surgical Instrument"; U.S. Pat. No. 5,152,744, entitled "Surgical Instrument"; U.S. Pat. No. 5,320,635, entitled "Surgical Device"; and U.S. Pat. No. 5,322,505, entitled "Surgical Instrument", all of which are incorporated by reference. Additional instruments are described in U.S. application Ser. No. 08/319,057, entitled "Surgical Instrument", which was filed on Sep. 23, 1994; U.S. application Ser. No. 08/425,719, entitled "Curved Surgical Instrument with Segmented Inner Member", which was filed on Apr. 20, 1995; U.S. application Ser. No. 08/388,992, entitled "Surgical Instrument", which was filed on Feb. 15, 1995; and U.S. application Ser. No. 08/200,662, entitled "Surgical Instrument", which was filed on Feb. 23, 1994, all of which are incorporated by reference.

In the illustrated embodiment, the surgical instrument 300 is a cutting instrument that includes a fixed hub 320 to which is attached a hollow outer tube 370, and a rotatable drive shaft 350 to which is attached a hollow inner tube 375. Openings in the distal ends of the tubes 370 and 375 have sharpened edges and perform a cutting action when the inner tube 375 is rotated within the outer tube 370. While hub 320 and drive shaft 350 are made from injection-molded plastic, tubes 370 and 375 are made from stainless steel to render the instrument readily disposable. Other materials could be used if it was desirable to make the instrument reusable.

Referring also to FIGS. 3A, 3B, 7A and 7B, drive shaft 350 includes an opening 380 that permits material drawn through inner tube 375 to pass into an aspiration channel 630 of the handpiece 100. The handpiece 100 also includes a handle 635 that controls a valve 640 and thereby controls flow through the aspiration channel 630. The handle 635 is positioned on the bottom of the handpiece near the distal end of the handpiece, and rotates about an axis 645 that is perpendicular to a longitudinal axis 140 of the handpiece. This orientation permits one-handed, finger control of flow through the aspiration channel 630 by a person holding the handpiece 100. The aspiration channel 630 ends at an aspiration spigot 650 at the proximal end of the handpiece. During use, the spigot 650 is connected to a source of suction (not shown).

Three knurled bands 655 define arcs about the circumference of the handpiece 100. These bands provide ease of gripping, and are formed by scoring the outer surface of the handpiece.

Figure 9A:
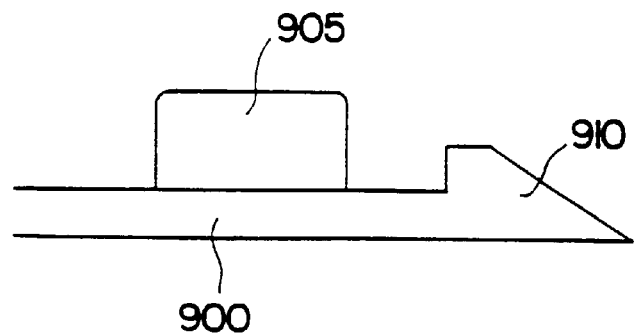
FIG. 9A is a side view of an alternative latching mechanism.

Other embodiments are also contemplated. For example, as illustrated in FIG. 9A, an alternative latching mechanism 900 includes a release button 905 that is axially spaced from a ramped latch 910. Due to the axial displacement, relatively more force must be incident on release button 905 to move ramped latch 910 than must be incident on release button 325 to move ramped latch 330 radially away from flange 610. To ease assertion of the additional force, release button 905 typically has a larger surface area than does release button 325. The axial displacement of the release button 905 relative to the ramped latch 910 permits the flange 610 to be moved proximally relative to the slot 605, which can be accomplished by shortening the slot, moving the flange, or a combination of the two. Movement of the flange relative to the slot eliminates the break in the flange due to the slot, while movement of the latch relative to the release button eliminates the break in the latch due to the release button. This permits the latch and flange to engage each other along continuous surfaces.

Figure 9B:
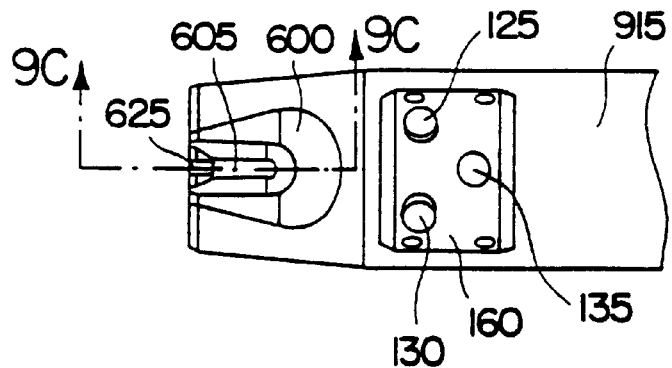
FIG. 9B is a top view of an end of a handpiece configured for interaction with the latching mechanism of FIG. 9A.
Figure 9C:
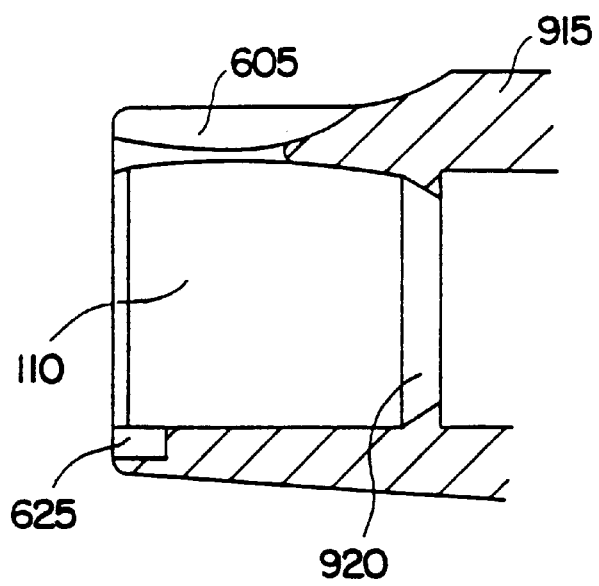
FIG. 9C is a sectional view of the handpiece end of FIG. 9B taken along section 9C—9C.

As shown in FIGS. 9B and 9C, a handpiece 915 for use with the latching mechanism 900 is identical to the handpiece 100 described above with the exception that the flange 920 of the handpiece 915 is positioned further from the distal end of the handpiece than is the flange 610 of the handpiece 100. In this configuration, the flange 920 is positioned proximally of the slot 605 within the bore 110 and no longer intersects the slot 605. Accordingly, the flange 920 is uninterrupted and forms a continuous ring around the interior of the bore 110. Similar results may be obtained by maintaining the position of the flange within the bore and shortening the slot 605.

Figure 9D:
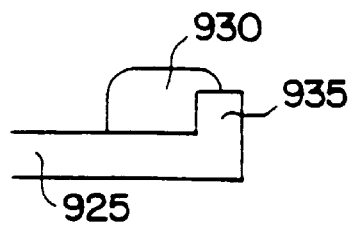
FIGS. 9D–9H are side and top views of other alternative latching mechanisms.
Figure 9E:
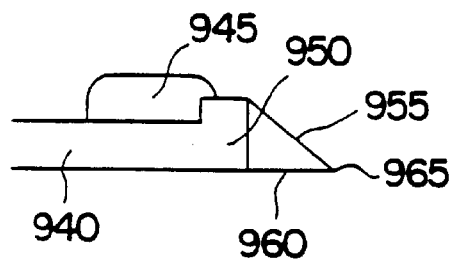
Figure 9F:
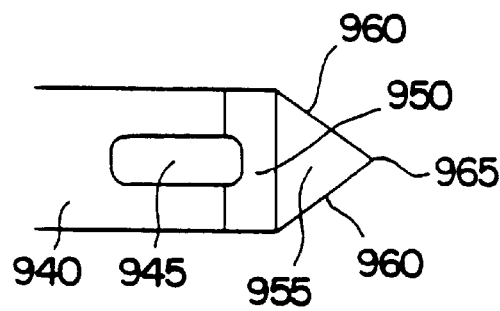
Figure 9G:
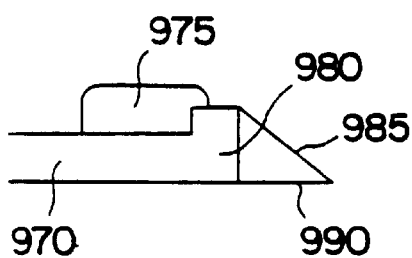
Figure 9H:
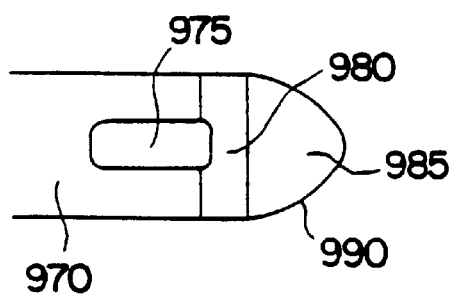

The latching mechanism 310 may also be varied in other ways. For example, FIG. 9D illustrates an alternative latching mechanism 925 that includes a release button 930 and a latch 935 having a square cross section. FIGS. 9E and 9F illustrate a latching mechanism 940 that includes a release button 945 and a ramped latch 950. In addition to having a ramped leading surface 955, the latch 950 includes a leading edge 960 that tapers to a point 965 in the longitudinal direction. Similarly, a latch 970 illustrated in FIGS. 9G and 9H includes a release button 975 and a latch 980 that includes a ramped leading surface 985 and a curved leading edge 990.

Figure 10A:
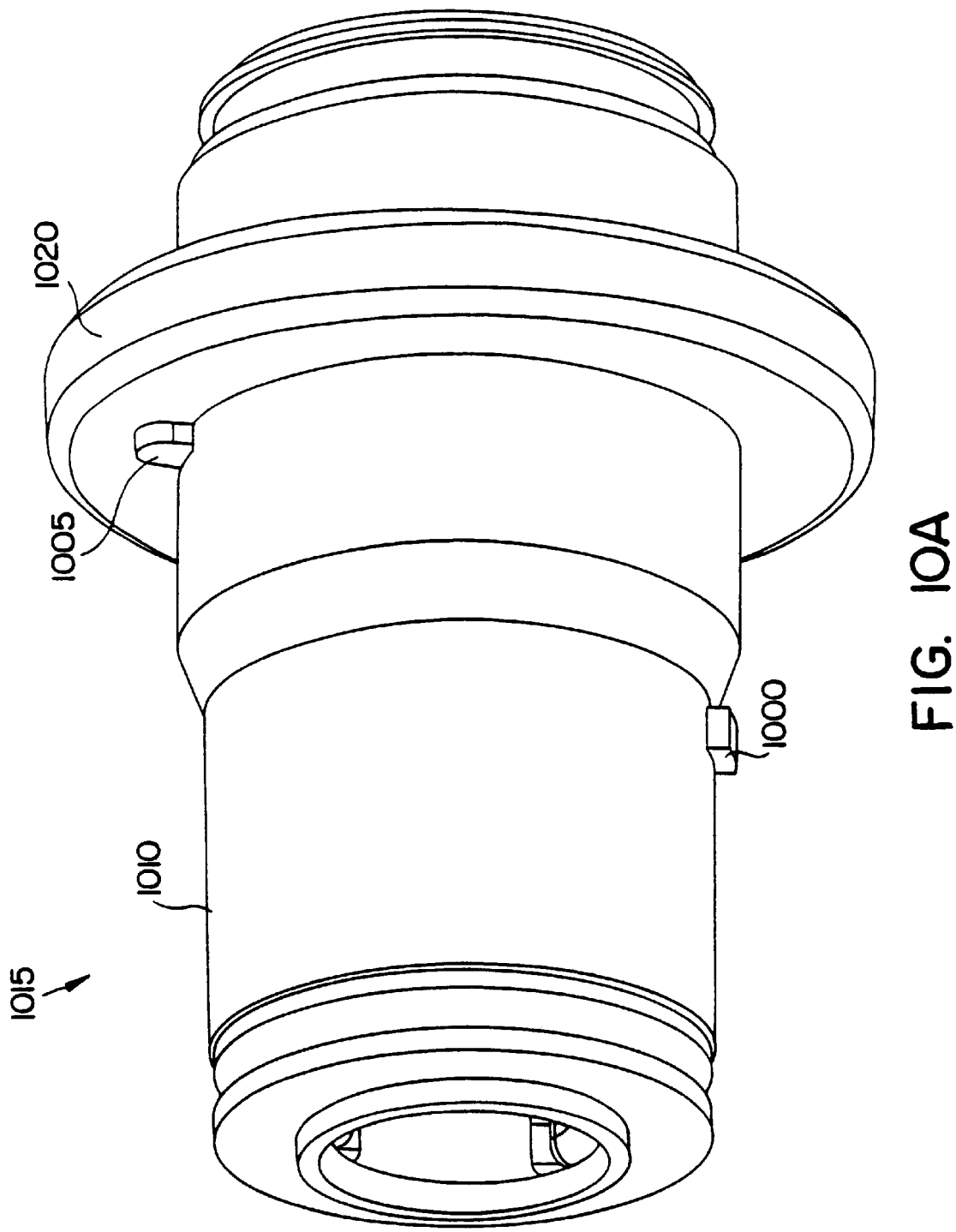
FIGS. 10A–10C are perspective and plan views of an alternative latching mechanism.
Figure 10B:
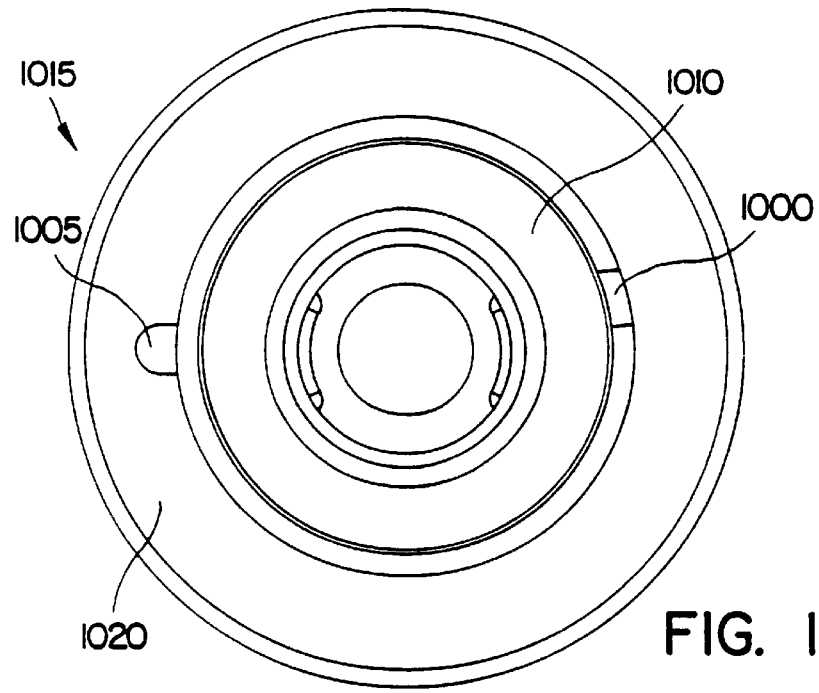
Figure 10C:
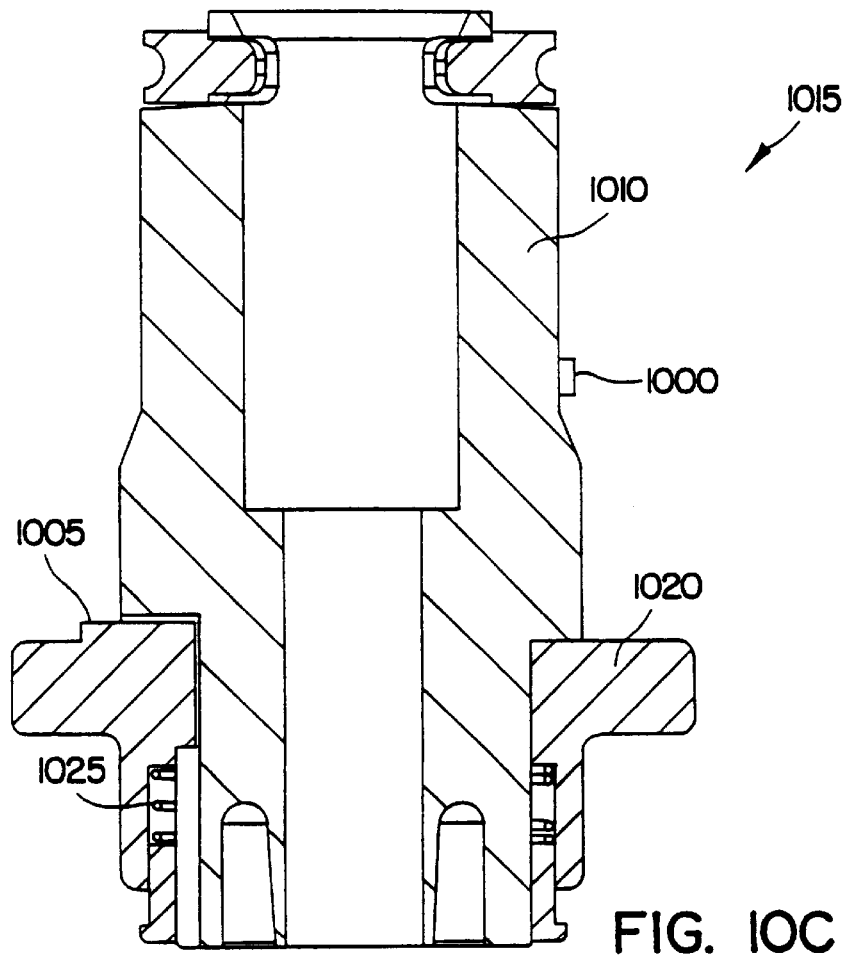

Referring to FIGS. 10A–10C, another alternative latching mechanism includes a tab 1000 and a tab 1005. Tab 1000 is mounted on a hub 1010 of a surgical instrument 1015. Tab 1005 is mounted on the proximal side of a spring-loaded plate 1020 that is positioned at the distal end of the hub 1010. Tabs 1000 and 1005 are positioned to define an arc on the order of 170° around the circumference of the hub 1010. At installation, the hub 1010 is inserted into the bore 110 of the handpiece, with the tab 1000 aligned with the slot 605. The hub is inserted until tab 1000 passes through the gap in the flange 610 that is formed by the slot 605. At that point, plate 1020 is pressed against the distal end of handpiece 100 so that a spring 1025 is compressed and, because the tabs 1000 and 1005 define an arc of 170° while slots 610 and 625 of the handpiece are offset by 180°, tab 1005 is not aligned with slot 625. Once the tab 1000 clears the gap, the hub 1010 is rotated until the tab 1005 aligns with the slot 625 and snaps into place to lock the hub 1010 within the bore. The instrument is removed from the bore by pulling the plate 1020 away from the handpiece 100 until the tab 1005 is out of the slot 625 and rotating the hub 1010 until the tab 1000 aligns with the gap in the flange 610.

Figure 11A:
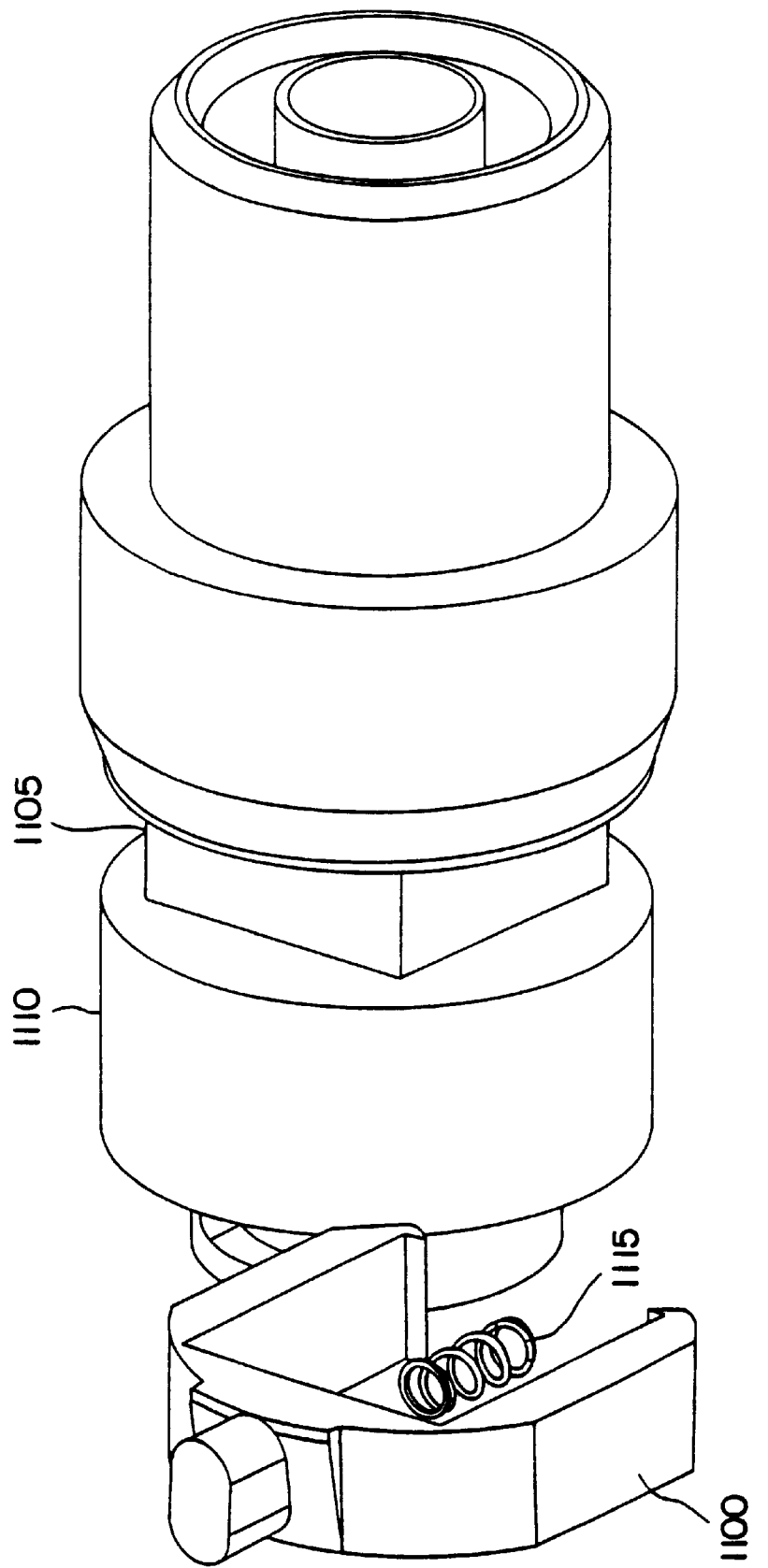

Referring to FIGS. 11A and 11B, the latching mechanism also may be implemented with a spring-loaded plunger 1100 positioned in an indentation 1105 in the hub 1110 of a surgical instrument. A spring 1115 could be a separate component or molded with the plunger 1100.

Referring to FIG. 12, the latching mechanism 310 also may be incorporated into an adapter 1200 for connecting a hub of a surgical instrument to a handpiece. The adapter 1200 includes a proximal end 1205 for insertion into the bore 110 of the handpiece and a distal end 1210 configured for attachment to a hub of a surgical instrument.

Other embodiments are within the following claims.

What is claimed is:

1. Apparatus comprising:
   a body configured for insertion into a bore of a surgical handpiece,
   a latch comprising a movable member connected to said body and having a latching structure configured to latchingly engage a surface of the surgical handpiece within the bore, the latch providing self-locking attachment of the body to the surgical handpiece without requiring user manipulation of the surgical handpiece or a movable portion of the apparatus, and
   a user-manipulable release portion connected to the apparatus and operable to disengage the latching structure from the surface of the surgical handpiece to permit removal of the body from the bore of the surgical handpiece.

2. A surgical device including the apparatus of claim 1, said surgical device further comprising the handpiece having a proximal end and a distal end, wherein said handpiece includes a bore at the distal end thereof for insertion of said body of said apparatus and an annular flange located within the bore to latchingly engage said latching structure when said body is inserted into said bore.

3. The surgical device of claim 2, wherein said handpiece includes a slot at the distal end thereof and wherein said latch further comprises a user-manipulable release portion positioned for insertion into said slot when said body is inserted into said bore.

4. The surgical device of claim 3, wherein said body includes a tab that extends radially from an exterior surface thereof and is positioned distally of said release portion, and wherein said handpiece includes an opening positioned for engagement with said tab when said body is inserted into said bore.

5. The surgical device of claim 2, wherein said annular flange includes a ramped edge at an end closest to the distal end of the handpiece and, at an end furthest from the distal end of the handpiece, an edge that is angled toward the distal end of the handpiece in a radial direction from a longitudinal axis of the bore.

6. The apparatus of claim 1, wherein said movable member comprises a cantilevered arm.

7. The apparatus of claim 6, further comprising a ring structure that carries said cantilevered arm and is secured to said body so that said arm extends proximally to and adjacent to an exterior surface of said body.

8. The apparatus of claim 7, wherein said ring structure is joined to a distal end of said body by a snap fit.

9. The apparatus of claim 6, wherein said cantilevered arm is configured to radially deflect during insertion into the bore of the handpiece and to return from the radial deflection to permit said latching structure to latchingly engage the surface of the surgical handpiece within the bore.

10. The apparatus of claim 3, wherein said user-manipulable release portion is mounted on said cantilevered arm.

11. The apparatus of claim 6, wherein said body is formed from a single piece of injection molded plastic.

12. The apparatus of claim 1, wherein said body includes a proximal end for insertion into the bore and wherein said latching structure includes:
   a leading edge that is ramped in a direction from the proximal end of said body toward a distal end of said body; and
   a latching surface oriented transversely to a longitudinal axis of said body.

13. The apparatus of claim 12, wherein said latching surface comprises a trailing edge at a distal end of said latching structure, said trailing edge being angled toward the distal end of said body in a radial direction from said body.

14. The apparatus of claim 1, wherein said body further comprises a tab that extends radially from an exterior surface thereof and is positioned to engage an opening in the handpiece.

15. The apparatus of claim 14, wherein said tab is positioned distally of said release portion.

16. The apparatus of claim 1, wherein said user-manipulable release portion is integrally mounted on the movable member.

17. The apparatus of claim 1, wherein said movable member is configured to radially deflect in response to pressure on said release portion so as to disengage said latching structure from the surface of the surgical handpiece within the bore.

18. The apparatus of claim 1, wherein said latching structure is positioned adjacent to said release portion.

19. The apparatus of claim 1, wherein said latching structure is spaced from said release portion along a longitudinal axis of said body.

20. The apparatus of claim 1, wherein said body is configured as a hub of a surgical instrument, said apparatus further comprising:
- an outer member connected to and extending from said body to a tissue receiving opening at a distal end of said outer member;
- an inner member including at a distal end thereof a surgical tool to cut tissue, said inner member being positioned within said outer member and being rotatable relative to said outer member; and
- a drive shaft connected to said inner member for rotating said inner member.

21. The apparatus of claim 1, wherein said body carries a magnet positioned to be sensed by a sensor of the surgical handpiece when said apparatus is inserted into the bore of the surgical handpiece.

22. The apparatus of claim 1, wherein said body comprises an adapter for interconnecting a hub of a surgical instrument to the handpiece, said adapter having a proximal end for insertion into the bore and a distal end configured for attachment to the hub of the surgical instrument.

23. A surgical device comprising:
- a handpiece having a proximal end and a distal end, wherein said handpiece includes a bore at the distal end thereof; and
- an apparatus including:
  - a body configured for insertion into a bore of a surgical handpiece,
  - a latch comprising a movable member connected to said body and having a latching structure configured to latchingly engage a surface of the surgical handpiece within the bore, the latch providing self-locking attachment of the body to the surgical handpiece without requiring user manipulation of the surgical handpiece or a movable portion of the apparatus, and
  - a user-manipulable release portion connected to the apparatus and operable to disengage the latching structure from the surface of the surgical handpiece to permit removal of the body from the bore of the surgical handpiece.

24. The surgical device of claim 23, wherein said movable member comprises a cantilevered arm.

25. The apparatus of claim 24, wherein said user-manipulable release portion is mounted on said cantilevered arm.

26. The apparatus of claim 25, wherein said movable member is configured to radially deflect in response to pressure on said release portion so as to disengage said latching structure from said surface of said surgical handpiece within the bore.

27. The surgical device of claim 26, wherein said handpiece includes a slot at the distal end for insertion of said user-manipulable release portion when said body is inserted into the bore.

28. The surgical device of claim 27, wherein said body includes a tab that extends radially from an exterior surface thereof and is positioned distally of said release portion, and wherein said handpiece includes an opening positioned for engagement with said tab when said body is inserted into said bore.

29. The surgical device of claim 24, wherein said movable member is configured to radially deflect during insertion into the bore of said handpiece and to return from the radial deflection to permit said latching structure to latchingly engage said surface of said surgical handpiece within the bore.

30. The surgical device of claim 23, wherein said handpiece further comprises an annular flange located within the bore to latchingly engage said latching structure when said body is inserted into the bore.

31. The surgical device of claim 30, wherein said body of said apparatus is configured as a hub of a surgical instrument, said apparatus further comprising:
- an outer member connected to and extending from said body to a tissue receiving opening at a distal end of said outer member;
- an inner member including at a distal end thereof a surgical tool to cut tissue, said inner member being positioned within said outer member and being rotatable relative to said outer member; and
- a drive shaft connected to said inner member for rotating said inner member.

32. The surgical device of claim 31, wherein said handpiece further comprises a motor having a drive shaft, and wherein said drive shaft of said surgical instrument includes an extension having sloped, canted edges at a proximal end of the extension for engagement with said drive shaft of said motor.

33. The surgical device of claim 30, wherein said annular flange includes a ramped edge at an end closest to the distal end of the handpiece and, at an end furthest from the distal end of the handpiece, an edge that is angled toward the distal end of the handpiece in a radial direction from a longitudinal axis of the bore.

34. The surgical device of claim 23, wherein said user-manipulable release portion is integrally mounted on the movable member.

35. The surgical device of claim 23, wherein said body of said apparatus comprises an adapter for interconnecting a hub of a surgical instrument to said handpiece, said adapter having a proximal end for insertion into the bore and a distal end configured for attachment to the hub of the surgical instrument.

* * * * *